(12) United States Patent
MacKinnon

(10) Patent No.: US 7,074,390 B2
(45) Date of Patent: Jul. 11, 2006

(54) ENCAPSULATED DENTIFRICE AND METHOD OF USE

(76) Inventor: Carol L. MacKinnon, 944 Purdue Dr., Woodland, CA (US) 95695

( * ) Notice: Subject to any disclaimer, the term of this patent is extended or adjusted under 35 U.S.C. 154(b) by 78 days.

(21) Appl. No.: 10/382,779

(22) Filed: Mar. 6, 2003

(65) Prior Publication Data

US 2004/0175334 A1    Sep. 9, 2004

(51) Int. Cl.
*A61K 8/00*    (2006.01)
*A61K 8/97*    (2006.01)
*A61C 15/00*    (2006.01)

(52) U.S. Cl. .................... 424/49; 424/58; 424/401; 424/451; 424/452; 424/456; 433/216; 206/528; 206/530; 206/531; 206/535; 206/536; 206/540; 221/229; 221/247

(58) Field of Classification Search .......... 424/401, 424/451, 452, 456, 49, 58; 433/216; 206/63.5, 206/528, 530, 531, 535, 536, 540; 221/229, 221/247
See application file for complete search history.

(56) References Cited

U.S. PATENT DOCUMENTS

| | | | | |
|---|---|---|---|---|
| 2,004,957 A | * | 6/1935 | Messner | 424/455 |
| 3,431,339 A | | 3/1969 | Gyarmathy et al. | |
| 3,902,509 A | * | 9/1975 | Tundermann et al. | 433/142 |
| 3,929,988 A | | 12/1975 | Barth | |
| 3,991,776 A | * | 11/1976 | Duffy | 132/311 |
| 4,171,753 A | * | 10/1979 | Vreede | 221/197 |
| 4,427,116 A | | 1/1984 | Brown | |
| 5,009,886 A | * | 4/1991 | Ahmad et al. | 424/58 |
| 5,057,305 A | | 10/1991 | Aberg | |
| 5,709,895 A | * | 1/1998 | Tanaka et al. | 426/96 |

* cited by examiner

*Primary Examiner*—Frederick Krass
(74) *Attorney, Agent, or Firm*—Mark J. Temmerman; Daniel P. Maguire

(57) ABSTRACT

A single use capsule containing dentifrice is disclosed. It includes toothpaste or other dentifrice enclosed in a shell or coating. The dentifrice may include miswak fibers, which acts as a natural brush, therefore obviating the need for a traditional brush. The coating may include choline and albumin. In use, a capsule is placed in the mouth, burst with the teeth, and then distributed throughout the mouth with the tongue. The teeth can then be brushed with a traditional brush, or the tongue can rub the miswak fibers over the teeth in lieu of using a brush.

5 Claims, 2 Drawing Sheets

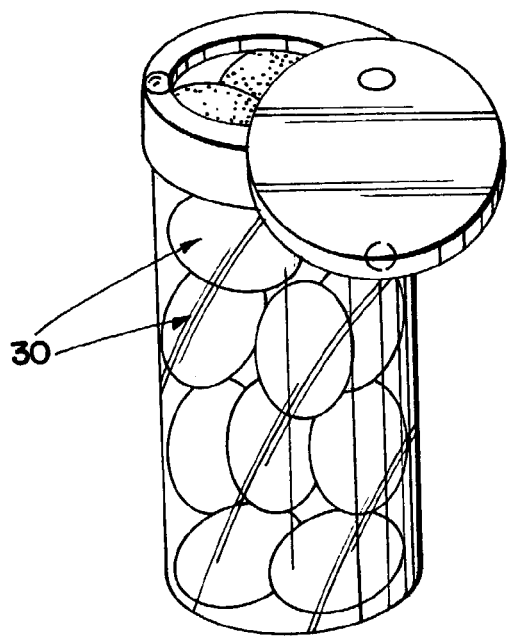
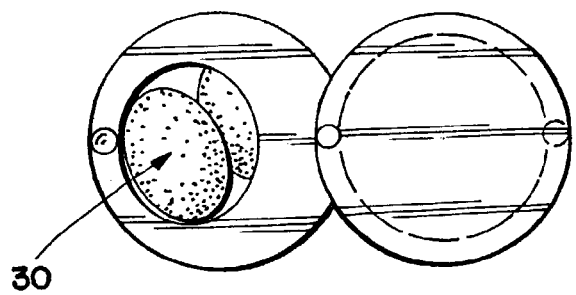
Fig. 5
Fig. 4
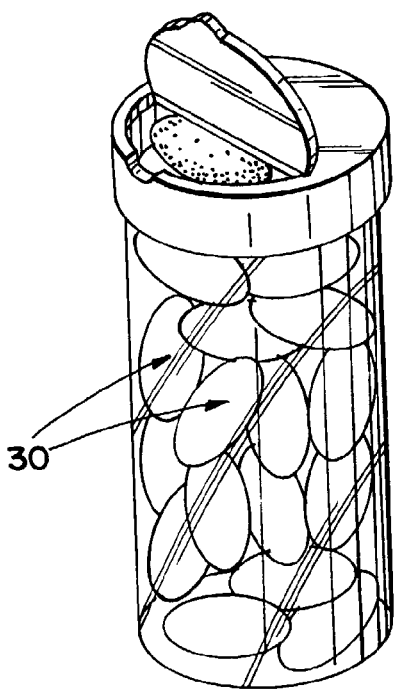
Fig. 6
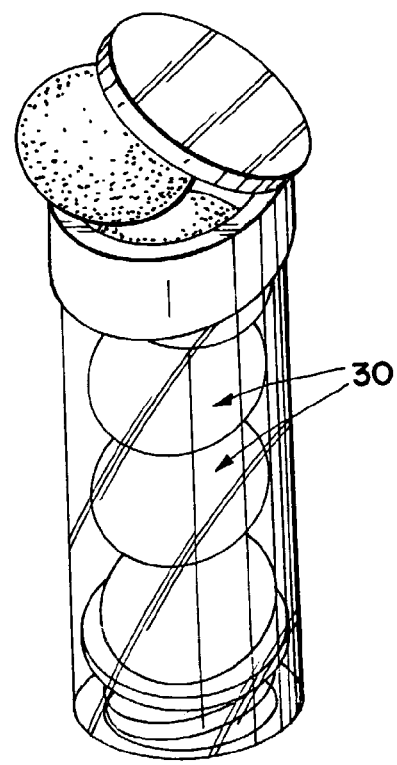
Fig. 7

ENCAPSULATED DENTIFRICE AND METHOD OF USE

BACKGROUND OF THE INVENTION

1. Field of the Invention

This invention relates to products for promoting oral hygiene.

2. General Background

Proper tooth brushing is essential for good dental health, but traditional tooth brushing techniques and products make if difficult to effectively clean the teeth.

First, many people do not spend enough time cleaning their teeth. Most dentists suggest brushing for two to four minutes, but studies indicate that many people only brush for 30 seconds or less.

Additionally, the traditional method of toothpaste application—placing the toothpaste on a brush and then putting the brush on the teeth—often results in uneven distribution of toothpaste around the mouth. The first area to be brushed typically gets too much toothpaste, and areas brushed later get too little. The portions that get too much toothpaste often experience unhealthy enamel wear, while the portions that receive too little are not effectively cleaned.

Also, traditional toothpaste containers are potentially wasteful, in that significant amounts of plastic and other materials must be used to hold a relatively small amount of toothpaste. Additionally, children are often reluctant to brush their teeth, and it would be desirable to make tooth brushing more entertaining for them.

Finally, tooth brushing obviously requires a brush, but travelers and others often forget or misplace their brushes, resulting in the vain attempt to brush the teeth with one's finger.

Therefore, there is a need for a dentifrice and dentifrice delivery method that makes it easier to brush one's teething for a sufficient amount of time, that facilities uniform application of toothpaste throughout the mouth, and that can be used with or without a toothbrush.

SUMMARY OF THE INVENTION

The present invention comprises a pre-measured amount of toothpaste encapsulated in a thin coating. The coating will dissolve or break in the user's mouth, thereby releasing the toothpaste for distribution throughout the mouth by the tongue or a toothbrush. The toothpaste may contain finely ground fibers of miswak, and these fibers, when circulated throughout the mouth by the tongue, will act as tiny brushes. Therefore, the product can be used without a toothbrush.

BRIEF DESCRIPTION OF THE DRAWINGS

FIG. 4 shows a rotating top dispenser holding encapsulated dentifrice units according to an embodiment of the present invention.

FIG. 5 is a top view of the rotating top container of FIG. 4.

FIG. 6 shows a flip-top container holding encapsulated dentifrice units according to an embodiment of the present invention.

FIG. 7 shows a spring-loaded dispenser holding encapsulated dentifrice units according to an embodiment of the present invention.

DETAILED DESCRIPTION

Figure 1:
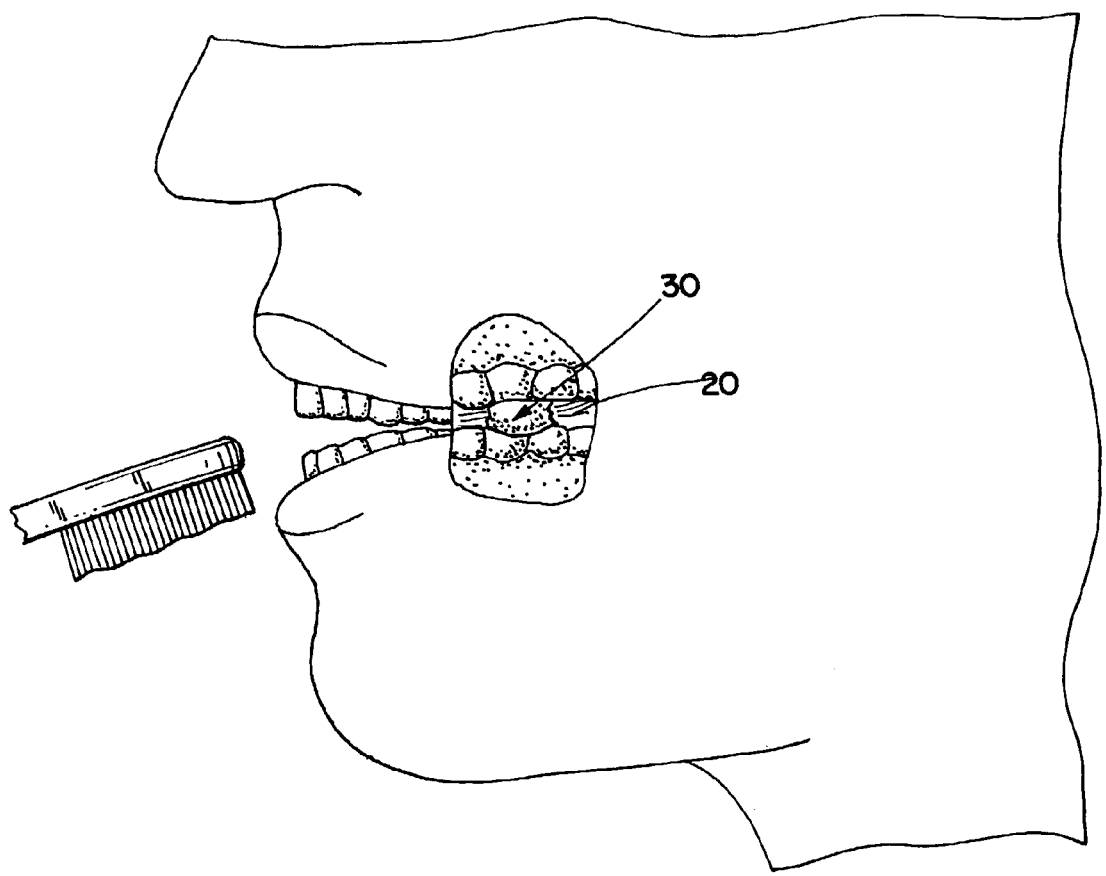
FIG. 1 is a cross-sectional view of a human subject biting into an encapsulated dentifrice according to an embodiment of the present invention.
Figure 2:
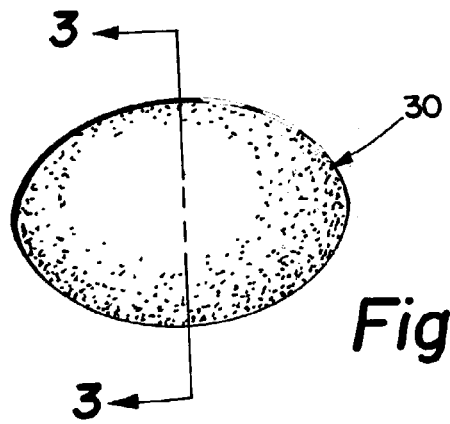
FIG. 2 is a perspective view of an encapsulated dentifrice according to an embodiment of the present invention.
Figure 3:
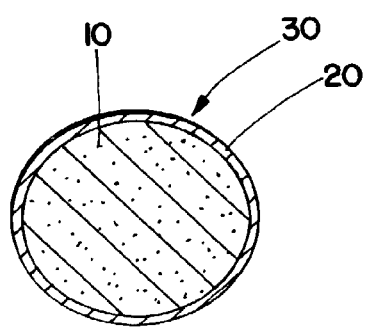
FIG. 3 is a cross-section of an encapsulated dentifrice according to the present invention, taken along line 3—3 in FIG. 2.

The present invention is dentifrice or toothpaste 10 encapsulated in a non-toxic shell or coating 20 to form a capsule 30. See FIGS. 1–3. The dentifrice 10 may be any toothpaste or other standard dentifrice. It may include a foaming agent, gelatin to help solidify the paste, whitening agents, baking soda, as well as traditional detergents. It also may include sweetening and flavoring agents, including honey and cinnamon powder. Additionally, it may include fluoride.

The dentifrice 10 may also include miswak fibers. Miswak is the root of the arak tree, which grows in Saudi Arabia, Sudan, Southern Egypt, Chad, and parts of India. Miswak has natural antiseptics, and it contains tannic acid, which has astringent qualities that protect the gums from disease.

The miswak fibers also can act as a type of brush, rubbing and cleaning the teeth. The fibers can be circulated throughout the mouth by the tongue, with the tiny miswak fibers replacing a traditional brush. The miswak fibers also can help freshen the breath and whiten the teeth.

The dentifrice 10 is covered with a thin coating or shell 20 to form a capsule 30. See FIG. 3. The shell 20 can be made of any number of nontoxic, biocompatible substances. In one embodiment, the coating or shell 20 would include choline, which also has nutritional benefits. The shell also may include egg whites, which contain the nutritious protein albumin. The egg whites form a colloidal solution when mixed with water, and therefore can be dispersed throughout the shell 20. Thus, in addition to encapsulating the toothpaste, the shell 20 can also provide nutritional benefits through the incorporation of choline and albumin. The shell 20 could also include gelatin, or a number of other conventional coatings that can be burst with the teeth or be dissolved with the saliva.

The capsules 30 can take a number of shapes and size, and in one embodiment it can be oval-shaped. See FIG. 2. The capsules should be sized to be large enough to contain a sufficient amount of toothpaste 10, but small enough to be easily inserted in the mouth. In one embodiment, each capsule would have a diameter of approximately, but not greater than, 0.5 inch.

The capsules 30 can be dispensed from a number of different types of containers. In one container, as shown in FIGS. 4 and 5, the top can rotate to reveal an opening large enough to dispense a single dentifrice unit. In another embodiment, the container could have a flip-top (see FIG. 6) for dispensing the capsules 30. In still another embodiment, the capsules 30 could be dispensed one at a time from a "Pez" type spring loaded dispenser. See FIG. 7.

In use, a capsule 30 could be taken from a dispenser, and put into the mouth. The coating 20 would then be broken with the teeth (see FIG. 1), and the toothpaste 10 could be distributed throughout the mouth using the tongue or a toothbrush. It would be preferable to distribute the toothpaste 10 throughout the mouth before brushing begins, to achieve uniform distribution.

If no toothbrush is available, the tongue and miswak fibers can act as a brush.

The present invention has a number of advantages over the prior art. First, it is easier to use than the very basic traditional method, which requires the user to unscrew or open the toothpaste tube, put the toothpaste on the brush, put the brush in the mouth, and then rescrew the tube. By contrast, with the present invention, the user only needs to pop the capsule in his/her mouth. This feature of the present invention makes it especially valuable for children, the disabled, and/or older individuals who may have difficulty unscrewing a toothpaste tube or putting toothpaste on the brush.

Second, the present invention helps avoid unnecessary waste, since the "packaging" for the toothpaste can simply be the coating.

Third, the present invention is convenient for travelers and others who may only need a small amount of toothpaste. Instead of taking an entire tube, a user can simply take the number of capsules that he/she will need.

Fourth, the present invention should make it easier to achieve uniform distribution of toothpaste, because the toothpaste can be distributed before the actual brushing begins. Indeed, since most people start brushing with the front of their mouth, those teeth get the most (and sometimes too much) toothpaste, while the back teeth get too little. With the present invention, the back teeth will get sufficient toothpaste, since most people will burst the capsule with their back teeth.

Fifth, the present invention may encourage individuals to brush longer, since they will need to spend less time getting ready to brush and therefore will have more time for actual brushing.

Sixth, the present invention may make tooth brushing more enjoyable for children, because of the novelty and fun in popping a capsule in one's mouth and bursting it. Of course, appropriate flavoring and novel marketing tools can be used to create specialized encapsulated toothpaste for small children.

Seventh, the present invention reduces the time needed for tooth cleaning, which makes it valuable for time-starved consumers. Not only does the present invention increase the speed at which all busy individuals can complete the "chore" of tooth brushing, but on those occasions when time is limited for traditional brushing, the miswak fibers of the present invention can continue the cleaning process after the traditional brushing has ended.

One skilled in the art will appreciate that the present invention can be practiced by other than the preferred embodiments, which are presented for purposes of illustration and not of limitation.

I claim:

1. A method of cleaning teeth, comprising:
   providing a capsule comprising
      a non-toxic saliva dissolvable shell defining a volume; and dentifrice inside said volume, said dentifrice comprising miswak fibers;
   placing said capsule in the mouth;
   releasing the dentifrice from said capsule;
   distributing the dentifrice around said teeth;
   cleaning the teeth with said dentifrice using only the tongue;
   dissolving said non-toxic saliva dissolvable shell in said mouth; and
   swallowing said non-toxic saliva dissolvable shell.

2. A method of cleaning teeth, comprising:
   providing a dentifrice comprising miswak fibers; wherein said dentifrice is encapsulated in a non-toxic saliva-dissolvable shell placing said dentifrice in the mouth; and cleaning the teeth with said dentifrice using only the tongue.

3. The method according to claim 2, wherein said non-toxic saliva-dissolvable shell comprises choline.

4. The method according to claim 2, wherein said non-toxic saliva-dissolvable comprises shell gelatin.

5. A method of cleaning the teeth consisting of steps 1) through 5):
   1) providing a dentifrice capsule comprising:
      a non-toxic saliva dissolvable shell defining a volume; and
      dentifrice inside said volume, said dentifrice comprising miswak fibers;
   2) placing said capsule in a mouth;
   3) bursting said capsule after it has been placed in the mouth, thereby releasing dentifrice into the mouth;
   4) dissolving said shell in saliva; and
   5) using a tongue to apply said dentifrice to teeth after bursting said capsule, thereby cleaning said teeth.

* * * * *

UNITED STATES PATENT AND TRADEMARK OFFICE
CERTIFICATE OF CORRECTION

| | | |
|---|---|---|
| PATENT NO. | : 7,074,390 B2 | Page 1 of 1 |
| APPLICATION NO. | : 10/382779 | |
| DATED | : July 11, 2006 | |
| INVENTOR(S) | : Carol Mackinnon | |

It is certified that error appears in the above-identified patent and that said Letters Patent is hereby corrected as shown below:

Title Page #74
The correct name should read Mathew J Temmerman.

Signed and Sealed this

Tenth Day of April, 2007

JON W. DUDAS
*Director of the United States Patent and Trademark Office*